United States Patent [19]
Varga et al.

[11] Patent Number: 5,440,031
[45] Date of Patent: Aug. 8, 1995

[54] 1,4,10,13-TETRAOXA-7,16-DIAZACYCLOOCTADECANE DERIVATIVES, PHARMACEUTICAL COMPOSITIONS CONTAINING THEM AND THEIR USE FOR THE REMOVAL OF TOXIC METAL IONS AND RADIOACTIVE ISOTOPES FROM LIVING ORGANISM

[75] Inventors: László Varga; László B. Sztanyik; Béla Kanyár; Ödön Király, all of Budapest; Ernö Brücher, Debrecen; József Emri, Debrecen; Béla Györi, Debrecen; Zoltán Kovács, Kisvárda, all of Hungary

[73] Assignees: Országos "Frederic Joliot-Curie" Sugár-biológiai és Sugáregészségügyi Kutató Intézet; Kossuth Lajos Tudományegyetem, Hungary

[21] Appl. No.: 102,955

[22] Filed: Aug. 6, 1993

Related U.S. Application Data

[63] Continuation of Ser. No. 761,345, Sep. 27, 1991, abandoned.

[30] Foreign Application Priority Data

Jan. 16, 1990 [HU] Hungary ................................ 145/90

[51] Int. Cl.⁶ ...................... C07D 225/02; A61K 9/02
[52] U.S. Cl. .................................. 540/465; 540/467; 424/464; 424/443; 424/45; 424/489; 424/451; 424/DIG. 15
[58] Field of Search ................ 540/467, 465; 514/184

[56] References Cited

U.S. PATENT DOCUMENTS 4,597,903 7/1986 Gokel et al. .................... 540/467
4,687,844 8/1987 Gokel et al. .................... 540/467

FOREIGN PATENT DOCUMENTS 2024822 1/1980 United Kingdom .

OTHER PUBLICATIONS

Chemical Abstracts, vol. 111, No. 15, Item No. 134408h.
Chemical Abstracts, vol. 111, No. 14, Item No. 125695x.
Chemical Abstracts, vol. 116, No. 10, Item No. 98085t.
Chemical Abstracts, vol. 115, No. 24, Item No. 269242c.

*Primary Examiner*—Thurman K. Page
*Assistant Examiner*—Raj Bawa
*Attorney, Agent, or Firm*—Keil & Weinkauf

[57] ABSTRACT

The invention relates to partially novel metal complexes, salts and double salts of 1,4,10,13-tetraoxa-7,16-diazacyclooctadecane compounds of the formula (I), $$\left[ M_r^{n+} \left| Q^1-N \quad Me_q^{p+} \quad N-Q^2 \right| N_s^{m+} \right] \quad (I)$$

wherein
$Q^1$ and $Q^2$ mean hydrogen or a group of the formula (III), $$\begin{array}{c} COO^- \\ | \\ -C-R \\ | \\ COO^- \end{array} \quad (III)$$

in the groups of the formula (III) the
R subtituents independently represent hydrogen, a $C_{1-5}$ straight or branched chain alkyl group, a $C_{2-5}$ straight or branched chain alkenyl group, phenyl or phenyl-$C_{1-5}$alkyl group, the two latter ones optionally being substituted on their aromatic part by one or more halogen(s), $C_{1-5}$alkyl, $C_{1-5}$alkoxy, cyano or nitro group(s), with the proviso that at least one of $Q^1$ and $Q^2$ is other than hydrogen;
Me stands for an alkaline metal or alkaline earth metal or transition metal ion;

(Abstract continued on next page.)

Abstract—continued q is 0 or 1;

M and N, independently from each other, stand for hydrogen or an alkaline metal, alkaline earth metal or optionally substituted ammonium ion;

m, n and p are integers each being equal to the charge of M, N or Me, respectively;

s and r are, independently from each other, 0, 1, 2, 3 or 4, with the proviso that (i) r, s and q cannot simultaneously be 0; and (ii) the number of hydrogens in the meaning of M or N may be 0, 1 or 2, which are useful in the decorporation of metal ions such as the radioactive isotopes of strontium or cerium and may be administered intravenously, locally, transdermally or rectally.

3 Claims, 4 Drawing Sheets

1,4,10,13-TETRAOXA-7,16-DIAZACYCLOOCTADECANE DERIVATIVES, PHARMACEUTICAL COMPOSITIONS CONTAINING THEM AND THEIR USE FOR THE REMOVAL OF TOXIC METAL IONS AND RADIOACTIVE ISOTOPES FROM LIVING ORGANISM

This application is a continuation of application Ser. No. 07/761,345, filed on Sep. 27, 1991, now abandoned.

The invention relates to partially novel 1,4,10,13-tetraoxa-7,16-diazacyclooctadecane derivatives and the use of such compounds for the decorporation of metal ions, mainly radioactive isotopes damaging the living organism. More particularly, the invention relates to metal complexes, salts and double salts of 1,4,10,13-tetraoxa-7,16-diazacyclooctadecane derivatives of the formula (I)

wherein

Q$^1$ and Q$^2$ mean hydrogen or a group of the formula (III), in the groups of the formula (III)

R substituents independently represent hydrogen, a C$_{1-5}$ straight or branched chain alkyl group, a C$_{2-5}$ straight or branched chain alkenyl group, phenyl or phenyl-C$_{1-5}$alkyl group, the two latter ones optionally being substituted on their aromatic part by one or more halogen(s), C$_{1-5}$alkyl, C$_{1-5}$alkoxy, cyano or nitro group(s), with the proviso that at least one of Q$^1$ and Q$^2$ is other than hydrogen;

Me stands for an alkaline metal or alkaline earth metal or transition metal ion;

q is 0 or 1;

M and N, independently from each other, stand for hydrogen or an alkaline metal, alkaline earth metal or optionally substituted ammonium ion;

m, n and p are integers each being equal to the charge of N, M or Me, respectively;

s and r are, independently from each other, 0, 1, 2, 3 or 4, with the proviso that (i) r, s and q cannot simultaneously be 0; and (ii) the number of hydrogens in the meaning of M or N may be 0, 1 or 2, as well as pharmaceutical compositions containing these compounds.

From the compounds of the formula (I), those containing hydrogen as Q$^1$ and Q$^2$ are used mainly as intermediates. When administered into the organism, the compounds of the formula (I), independently whether they are new or not, are capable to form a stable complex with radioactive metal ions, above all with radioactive strontium and cerium being present in the blood circulation and extracellular space, and then to be eliminated.

From the compounds of the formula (I), the novel ones contain a group of the formula (III), wherein either R is other than hydrogen; or, q is 1 when R is hydrogen, i.e. the complexes; further, wherein M and N are other than sodium or lithium ion when q is 0.

Thus, on the one hand, the present invention relates to compounds of the formula (I), wherein Q$^1$ and Q$^2$ mean hydrogen or a group of the formula (III), with the proviso that at least one of them is other than hydrogen; and in the groups of the formula (III) the R substituents independently mean hydrogen, a C$_{1-5}$ straight or branched chain alkyl group, a C$_{2-5}$ straight or branched chain alkenyl group, phenyl or phenyl-C$_{1-5}$alkyl group, the two latter ones optionally being substituted on their aromatic part by one or more halogen(s), C$_{1-5}$alkyl, C$_{1-5}$alkoxy, cyano or nitro group(s);

Me stands for an alkaline metal or alkaline earth metal or transition metal ion;

q is 0 or 1;

M and N, independently from each other, stand for hydrogen or an alkaline metal, alkaline earth metal or optionally substituted ammonium ion;

m, n and p are integers each being equal to the charge of N, M or Me, respectively;

s and r are, independently from each other, 0, 1, 2, 3 or 4, with the proviso that (i) r, s and q cannot simultaneously be 0;

(ii) the number of hydrogens in the meaning of M or N may be 0, 1 or 2;

(iii) q is 1 when R means hydrogen; and (iv) M and N are other than sodium or lithium ions when q is 0.

Returning to the substituents of the formula (I), R as a C$_{1-5}$alkyl group may be of straight or branched chain such as a methyl, ethyl, n-propyl, isopropyl, n-butyl, sec-butyl, tert-butyl, n-pentyl or isopentyl group, preferably a methyl or ethyl group; R as a C$_{2-5}$alkenyl group may be e.g. a vinyl or propenyl group; R as phenyl-C$_{1-5}$alkyl group may contain one of the alkyl moieties defined above, preferably a methyl group.

Me as an alkaline metal ion means preferably sodium or potassium ion; Me as an alkaline earth metal ion preferably stands for calcium or magnesium ion; and Me as a transition metal ion may be e.g. the ion of a metal belonging to the 3d, 4d or 5d group, preferably iron(II) (ferrous) or zinc ions. M and N as alkaline metal or alkaline earth metal ions are preferably the above ions; whereas the optionally substituted ammonium ion contains 1,2,3 or 4 above-identified alkyl, phenyl or phenylalkyl group(s) (supposed that no steric hindrance occurs). Due to their toxicity, the compounds containing a tetramethylammonium ion, cannot be used for administering into a living organism.

It is known that, on nuclear explosions or nuclear reactor disasters, very dangerous radioactive isotopes such as iodine-131 ($^{131}$I), strontium-89 and -90 ($^{89}$Sr and $^{90}$Sr) as well as cesium-134 and -137 ($^{134}$Cs and 137Cs) and cerium-$^{141}$ and -144 ($^{141}$Ce and $^{144}$Ce) may get into the atmosphere/see e.g. in: Nuclear and Radiochemistry", John Wiley and Sons, pages 158 to 166 (1981/.

When these isotopes get to the lungs by inhalation or to the digesting tract by intake of contaminated food or fluid or to the blood circulation or lymphatic system after resorption through the skin, they are deposited and accumulated in the tissues and finally, they lead to severe health injuries/"Summary Report on the Post Accident Review Meeting on the Chernobyl Accident" Safety Series No. 75, IAEA, Vienna (1986)/.

After the radioactive contamination, strontium begins to be built in to the bones in several hours, and there is no more possibility to elinimate (decorporate) the strontium deposited from the organism. Thus, the protection against radioactive strontium is particularly problematic.

The only possible way of protection is to inhibit the fixation of strontium to the tissues, above all to bone tissues by introducing a suitable strontium-specific complexing agent to the organism, thus binding in a stable form the isotope occuring in the blood circulation or extracellular space and decorporating it from the organism.

The solving of this problem is made more difficult thereby that the calcium complexes of complexing agents known from the literature, e.g. ethylenediaminetetraacetic acid or diethylenetriaminepentaacetic acid, are substantially more stable than their strontium complexes/A. Catsch: "Radioactive Metal Mobilization in Medicine", Ed. Charles C. Thomas, Springfield, Ill. (1964); A. Catsch: "Dekorporierung radioaktiver und stabiler Metallionen", Therapeutische Grundlagen, Ed. Thiemig, Munich (1968); A. Catsch: "Removal of Transuranium Element by Chelating Aoents", in: Diagnosis and Treatment of Incorporated Radionuclides, IAEA Publication No. STI/PUB/411, IAEA, Vienna, page 295 (1976)/.

A new possibility for the research has been recognized by the synthesis of the crown ether and cryptand type molecules. Namely, the mechanism of complex formation is in this case different from that of the earlier known complexing agents as due to the structure of the new complex forming molecule, the metal ions get to holes with well-defined sizes and therefore, the stability of the complex formed essentially depends on the size of the metal ion.

The first promising results were obtained during the investigations on 4,7,13,16,21,24-hexaoxa-1,10-diszabicyclo/8,8,8/hexacosane forming s strontium complex with a stability constant of several orders of magnitude higher than that of its calcium complex/"Coordination Chemistry of Macrocyclic Compounds", Ed. G. A. Melson, Plenum Press (1979)/. However, by using this compound in animal experiments it could only be proven that the complex formed with the ligand outside the organism was not dissociated in the organism after administration, but no evidence was obtained that radioactive strontium could be removed from the organism as a stable complex formed with the ligand. In addition, the ligand proved to be highly toxic/W. H. Müller: Naturwiss. 57 248 (1970); W. H. Müller and W. A. Müller: Naturwiss. 61, 455 (1974); W. H. Müller et al.: Naturwiss. 64, 96 (1977); J. Knajfl et al.: 12th Ann. Meeting of ESRB, Budapest (1976); J. Batsch et al.: Nukleonika 23, 305 (1978).

The compounds of the formula (I), being salts when q is 0 and complexes when q is 1, possess specific complexing properties enabling them to bind and decorporate metal ions being harmful to the organism, mainly the radioactive strontium and cerium getting to the living organism and being present in the blood circulation as well as in the extracellular space of the organism.

By administering the pharmaceutical compositions containing the compounds of the formula (I) as active ingredients to humans or animals, the depositions of the radioactive strontium into tissue parts can be prevented and thereby severe health injuries induced by the radiation load of the organism can be avoided or diminished.

F. de Jong et al. published a method for the preparation of N,N'-bis(dicarboxymethyl)-1,4,10,13-tetraoxa-7,16-diazacyclooctadecane tetralithium salt/Rec. Trav. Chim. Pays-Bas 102, 164 (1983)/. According to this method, the corresponding cryptand was reacted with methyl 2-bromomalonate and the ester derivative obtained was hydrolyzed to give the lithium salt in a yield of not more than 15%. According to the British patent specification No. 2,024,822 the lithium salt thus prepared can be used in the form of a composition being useful for enhancing the solubility of barium sulfate in the petroleum industry. The corresponding tetrasodium salt is also mentioned in the same specification although it is not described in a specific example. The double salt of the tetrasodium salt with sodium bromide as well as the therapeutic utility of this double salt have been published in the Hungarian patent application No. 2614/89.

The water-soluble salts and complexes of formula (I) according to the invention, wherein $Q^1$, $Q^2$, R, Me, M, N, m, n, p, r, s and q are as defined above, can be prepared on the analogy of the reaction mentioned above by reacting the corresponding halogenated dicarboxylic acid of the formula (II), wherein R is as defined above and X stands for halogen, preferably bromine, or a reactive derivative, suitably an ester, thereof with 1,4,10,13-tetraoxa-7,16-diazacyclooctadecane in an organic solvent medium and then hydrolyzing the thus-obtained product by a strong base, e.g. sodium hydroxide or by a mixture of suitable molar ratio of a strong base and a hydroxide or salt, preferably a halide, of a complex-forming metal.

Alternatively, the water-soluble salts and complexes of the compounds of the formula (I), wherein M and N stand for hydrogen or an alkaline metal or alkaline earth metal ion and Me means an alkaline earth metal ion, can be synthetized also by reacting 1,4,10,13-tetraoxa-7,16-diazacyclooctadecane with a 2-halodicarboxylic acid of formula (II) preferably with 2-bromomalonic acid in an aqueous medium at a pH of 6 to 13 in the presence of the alkaline metal or alkaline earth metal hydroxide corresponding to the salt to be prepared.

The complexes of formula (I), wherein q is 1, can be obtained by reacting an alkaline metal salt of the formula (I), wherein q is 0 and M as well as N stand for alkaline metal ions, preferably the tetrasodium salt, with an equivalent amount of a complex-forming metal halide, suitably metal chloride.

The action of the compounds of formula (I) according to the invention, which manifests itself as an increase in the elimination of metal ions damaging the living organism, was investigated by using radioactive strontium or cerium ions on Swiss mice and Wistar rats of both sexes.

The elimination was studied on radioactive isotopes introduced in various routes to various sites, e.g. to the blood circulation, abdominal cavity, lungs, muscles or subcutaneous connective tissue of the experimental animals. The compound increasing the elimination of the isotopes was administered daily once or two times in the form of an injection, powder or liquid aerosol or plaster to the organism of the experimental animals. Thereafter, whole body activity measurements were performed and retention curves were taken up which then were compared to the results obtained in the control group.

The retention curves obtained were analysed on a computer. "Nonlinear Regression by the Code of BMDP-3R" (BMDP Statistical Software Manual, UCLA, Los Angeles, 1990, Chief Ed. W. J. Dixon) computer software was used for this purpose. It could be stated from the results obtained that the curves could be described by a two-component descending exponential function. Two data were calculated for characterizing the effectivity. One of these was the so-called F factor indicating the increase in the elimination in relation to the control and meaning the multiplication of the isotope elimination under effect of the test compound in relation to the untreated animals/see column (C) in Table 1/.

For the illustrative comparison of the compounds according to the invention additional characteristic data, the so-called EI values are given which were obtained by multiplying the extent of isotope elimination as percentage related to the control group (effectivity, E) with the acute toxicity value ($LD_{50/30}$, innocuous, I)/see column (D) in Table 1/. Although the EI value is numerically not identical to the therapeutic ratio (safety index), it indicates in all cases to a weak or excellent activity of a product.

It is considered to be an important experimental observation that no radioactive strontium if any could be detected in the bones of the animals treated with an active compound of the invention; a residual activity of 5 to 10% measured as whole-body retention was found in the soft parts and liver of the animals whereas a major part (65 to 70%) of the retention measured in the organism of the control animals was built in to the bones.

Similar results were obtained by administering the test compounds in various routes to the organism.

It has been proven that an excellent effectivity was shown by compounds of the formula (I), wherein $Q^1$ and $Q^2$ are the same and R stands for hydrogen. From these compounds N,N'-bis(dicarboxymethyl)-1,4,10,13-tetraoxa-7,16-diazacyclooctadecane calcium complex disodium salt showed a particularly outstanding effect. The importance of the effective compounds of formula (I) is further pronounced by their very advantageous therapeutic ratio. Due to its low toxicity and high decorporating effectivity, the calcium complex disodium salt mentioned above is particularly preferred.

The compounds of formula (I) can be converted to pharmaceutical compositions by using the common carriers and other auxiliary materials in a known manner. The useful carriers, excipients, disintegrating, binding and other additive materials are described in detail in a number of relating handbooks.

The investigations on the effectivity of the compounds of Examples 1 to 16 showed that, after administration, the active ingredient was absorbed and exerted a decorporating effect either in the form of an injectable solution or in the form of a sublingual tablet, dragée, capsule, entero-solvent tablet, powder or liquid aerosol or transdermal plaster. The effective dose was found to be 1.0 to 200 µmol/kg of body-weight, preferably 10 to 100 µmol/kg of body-weight, which was administered in one or more portions, preferably in two subdoses.

The pharmaceutical compositions containing the compounds of formula (I) as active ingredient are useful also for the prevention of building-in to the organism of metal ions being harmful to the living organism.

The invention is illustrated in detail by the aid of the following non-limiting Examples.

EXAMPLE 1

Preparation of N,N'-bis(dicarboxymethyl)-1,4,10,13-tetraoxa-7,16-diazacyclooctadecane tetrasodium salt a) 2.74 g (14.98 mmol) of 2-bromomalonic acid are neutralized in 1.0 ml of water by adding sodium hydroxide solution of 7.410 mole/liter concentration in the presence of phenolphthalein indicator. Then 1.75 g (3.69 mmol) of N-dicarboxymethyl-1,4,10,13-tetraoza-7,16-diazacyclooctadecane disodium salt containing 14.10% by weight of sodium bromide (intermediate) obtained in a preceding reaction, then 1.95 g (7.43 mmol) of 1,4,10,13-tetraoxa-7,16-diazacyclooctadecane are added to the above solution. The reaction mixture is maintained at 60° C. for 10 to 11 hours while adding 2,02 ml of sodium hydroxide solution of 7.410 mole/liter concentration (14.98 retool) in 0.1 ml portions. After termination of the reaction the solution is filtered off when necessary, sodium bromide is added, then it is evaporated, dried under reduced pressure and extracted in several portions with a total of 20 to 25 ml of methylene chloride.

The extract is evaporated to dryness, 10 to 15 ml of petroleum ether are added and after filtration the precipitate is dried in a stream of nitrogen. 2.27 g (4.82 mmol) of the product obtained containing 13.3% by weight of sodium bromide (intermediate) are used in the next manufacturing production batch.

The identifying data of the intermediate are as follows: $^1$H-NMR spectrum (200 MHz, $D_2O$, δ ppm): 3.87 (1H, s); 3.67 (18H, m); 2.78–2.92 (8H, m).

The residue of the methylene chloride extract is extracted with 60 ml of anhydrous ethanol until the extract is practically free from solid material. The residue of the extraction is dissolved in 6 to 7 ml of water and after adding sodium bromide it is evaporated to dryness and dried. Thereafter, it is extracted by using 30 ml of anhydrous ethanol as described above. The two ethanolic extracts are combined and evaporated to dryness to give 4.89 g of double salt containing 2.71 moles of sodium bromide. The yield is 94.1% calculated for the macrocycle used.

The identifying data for the double salt are as follows: IR spectrum (KBr, cm$^{-1}$): 2950, 2868 (m, $\gamma_{C\text{-}H}$); 1605 (vs, $\gamma_{COO/as}$); 1430 (m, $\gamma_{COO/s}$). Other characteristic but unidentified frequencies: 1350 (s), 1320 (s), 1095 (s), 928 (w). $^1$H-NMR spectrum (200 MHz, D$_2$O, δ ppm): 4.00 (2H, s); 3.70 (8H, s); 3.63 (8H, t); 2.92 (8H), t).

b) Sodium bromide is removed from the double salt by extraction with 50 ml of 95% by weight ethanol. The extraction residue is dried and made free from ethanol under reduced pressure to give 3.22 g of product. The yield is 93.24% calculated for the macrocycle used.

The identifying data of the product are as follows: $^1$H-NMR spectrum (200 MHz, D$_2$O, δ ppm): 3.95 (2H, s); 3.64 (8H, s); 3.60 (8H, t); 2.85 (8H, t). $^{13}$C-NMR spectrum (50 MHz, D$_2$O, δ ppm): 179.95 (C=O); 76.45 (N-CH-(COO)$_2$); 71.66 and 70.84 (O-CH$_2$); 54.06 (N-CH$_2$).

EXAMPLE 2

Preparation of N,N'-bis(dicarboxymethyl)-1,4,10,13-tetraoxa-7,16-diazacyclooctadecane tetrasodium salt containing disodium hydroxy malonate The process described in Example 1 is followed by using 2.84 g (15.54 mmol) of 2-bromomalonic acid, 2,02 g (4.11 mmol) of N-dicarboxymethyl-1,4,10,13-tetraoxa-7,16-diazacyclooctadecane disodium salt containing 16.87% by weight of sodium bromide and 2.01 g (7.66 mmol) of 1,4,10,13-tetraoxa-7,16-diazacyclooctadecane, except that the reaction mixture is maintained at 50° C. and the sodium hydroxide is portionwise added during 10 hours. The amount of monosubstituted intermediate obtained-by extraction with methylene chloride is 2.17 g (4.41 mmol) and contains sodium bromide in an amount of 16.93% by weight. The product weighes 3.92 g, the yield is 96.5% calculated for the macrocycle used. The product contains 1.6% by weight of disodium hydroxymalonate.

The $^1$H-NMR spectrum of the product (200 MHz, D$_2$O, δ ppm) agrees with that of the product of Example 1, except that a resonance signal also appears at 4.31 (s) which is characteristic of hydroxymalonate.

EXAMPLE 3

Preparation of N,N'-bis(dicarboxymethyl)-1,4,10,13-tetraoxa-7,16-diazacyclooctadecane tetrapotassium salt a) After neutralizing 1.32 g (7.22 mmol) of 2-bromomalonic acid in 1.0 ml of water by adding potassium hydroxide solution of 5.760 mole/liter concentration in the presence of phenolphthalein indicator, 1.25 g (4.77 mmol) of 1,4,10,13-tetraoxa-7,16-diazacyclooctadecane are added. The reaction mixture is heated at 50° C. for 26 hours while adding an equivalent amount of potassium hydroxide solution of 5.760 mole/liter concentration in portions. After evaporating the reaction mixture the solid residue is dried under reduced pressure and then extracted with a total of 20 ml of methylene chloride in several portions. After evaporation the residue is dried to give 0.85 g (1.73 mmol) of N-dicarboxymethyl-1,4,10,13-tetraoxa-7,16-diazacyclooctadecane dipotassium salt containing 16.7% by weight of potassium bromide (intermediate). This product can be used in a next manufacturing batch.

The residue of the methylene chloride extraction is extracted with 60 ml of anhydrous ethanol and after evaporation of the extract the residue is dried to give 2.18 g of product, i.e. a yield of 94.0% calculated for the macrocycle used.

The product is a double salt formed with potassium bromide which contains 29.97% by weight of potassium bromide. $^1$H-NMR spectrum of the intermediate (200 MHz, D$_2$O, δ ppm): 3.86 (1H, s); 3.63 (16H, m); 2.89 (4H, t); 2.78 (4H, m). $^1$H-NMR spectrum of the double salt formed with potassium bromide (200 MHz, D$_2$O, δ ppm): 3.99 (2H, s); 3.69 (8H, s); 3.63 (8H, t); 2.86 (8H, t).

b) A pure potassium bromide-free product can be prepared by extracting the product obtained as described above with 97% by volume ethanol to give 1.16 g of product, i.e. a yield of 75.6% calculated for the macrocycle used. $^1$H-NMR spectrum of the title product (200 MHz, D$_2$O, δ ppm): 4.00 (2H, broad s); 3.70 (8H, broad s); 3.65 (8H, broad); 2.88 (8H, broad).

EXAMPLE 4

Preparation of N,N'-bis(dicarboxymethyl)-1,4,10,13-tetraoxa-7,16-diazacyclooctadecane magnesium complex disodium salt 0.30 g (1.46 mmol) magnesium chloride hexahydrate dissolved in 2.0 ml of water is added to a solution containing 0.81 g (1.46 mmol) of product prepared according to Example 1 b) in 3.0 ml of water. After 30 minutes the solution is evaporated under reduced pressure and the residue is dried to give 0.93 g (97.8%) of title product containing 17.99% by weight of sodium chloride.

$^1$H-NMR spectrum of the title product (200 MHz, D$_2$O in the presence of NaOD, δ ppm): 4.00 (2H, s); 3.67 (8H, s); 3.62 (8H, broad); 2.88 (8H, broad). $^{13}$C-NMR spectrum (50 MHz, D$_2$O, δ ppm): 179.71 (C=O); 71.88 and 71.05 (O-CH$_2$); 54.51 (N-CH$_2$). Note: due to deuteration the resonance signal of CH(COO)$_2$ is absent.

EXAMPLE 5

Preparation of N,N'-bis(dicarboxymethyl)-1,4,10,13-tetraoxa-7,16-diazacyclooctadeoane calcium complex disodium salt containing sodium chloride The process described in Example 4 is followed by using 0,92 g (1.65 mmol) of product obtained according to Example 1 b) and 0.24 g (1.65 mmol) of calcium chloride dihydrate to give 1.08 g (98.2%) of title product containing 17.57% by weight of sodium chloride.

$^1$H-NMR spectrum of the product (200 MHz, D$_2$O, δ ppm): 3.90 (4H, broad); 3.53 (14H, broad); 2.92 (4H, coalesced t); 2.72 (4H, coalesced t). $^{13}$C-NMR spectrum (50 MHz, D$_2$O, δ ppm): 179.23 (C=O); 82.38 (CH(COO)$_2$); 71.62 (O-CH$_2$); 55.63 (N-CH$_2$).

EXAMPLE 6

Preparation of N,N'-bis(dicarboxymethyl)-1,4,10,13-tetraoxa-7,16-diazacyclooctadecane calcium complex disodium salt containing disodium hydroxymalonate and sodium chloride After neutralizing 3.44 g (18.825 mmol) of 2-bromomalonic acid in 1.0 ml of water by adding sodium hydroxide solution of 8.360 mole/liter concentration in the presence of phenolphthalein indicator, 2.010 g (7.65 mmol) of 1,4,10,13-tetraoxa-7,16-diazacyclooctadecane are added. The reaction mixture is heated at 30 to 45° C. for 43 to 48 hours while adding sodium hydroxide solution (1.83 ml) required to form the disubstituted compound. Thereafter, the reaction mixture is maintained at 60° C. for 22 to 25 hours while portionwise adding sodium hydroxide solution in an amount required to hydrolyze the unreacted 2-bromomalonate. After termination of the reaction the solution is evaporated, then Example 1 b) is followed to obtain 4.720 g of dry crude product containing 12.0% by weight of disodium malonate and practically no sodium bromide. The crude product may be worked up in any of the following two ways:

a) The crude product is dissolved in a mixture of 3.0 ml of water and 7.5 ml of calcium chloride solution of 1.000 mole/liter concentration. 12.0 ml of 99.7% by volume ethanol and 0.85 ml of calcium chloride are added to the above solution under stirring, then the ethanol content of the solution is adjusted to 90% by volume by adding 105 ml of 99.7% by volume ethanol. After vigorously stirring the suspension obtained for 30 to 60 minutes with heating and then filtering off the solid precipitate, the filtrate is evaporated under reduced pressure and the half-dry product is dried at 75° to 85° C. under reduced pressure to give 4.48 g (90.6%) of the title product containing 14.0% by weight of sodium chloride and 1.08% by weight of disodium hydroxymalonate.

The $^1$H-NMR spectrum of the product (200 MHz, $D_2O$, δ ppm) is in agreement with that of the product of Example 5, except that a resonance signal also appears at 4.31 ppm (1H, s) which is characteristic of hydroxymalonate.

b) The crude product is worked up as described under a) above, except that after adding the first portion (7.50 ml) of the calcium chloride solution an additional portion of 3.10 ml of calcium chloride solution of 1.000 mole/liter concentration is added to the reaction mixture, the ethanol content of the mixture is adjusted to 90% by volume by adding 114 ml of ethanol and the product is dried in nitrogen stream to give 5.00 g (94.9%) of product containing also 19.5 mol % of calcium salt of the calcium complex (as calculated for the total of macrocycle) in addition to the disodium salt of the calcium complex.

The product contains 13.2% by weight of sodium chloride, 7.35% by weight of water and a negligible amount of disodium hydroxymalonate.

The $^1$H-NMR spectrum of the product (200 MHz, $D_2O$, δ ppm) is in agreement with that of the product of Example 5.

EXAMPLE 7

Preparation of N,N'-bis(dicarboxymethyl)-1,4,10,13-tetraoxa-7,16-diazacyclooctadecane calcium complex diammonium 0.5 ml of water, 2.04 ml of 0.998 mole/liter calcium chloride solution and then 30 ml of anhydrous ethanol are added to 0.554 g (1.000 mmol) of tetrasodium salt obtained according to Example 1 b). The solution is evaporated to about the third of its original volume and anhydrous ethanol is added in a sufficient amount to adjust the ethanol concentration of the solution to 95–96% by volume. Thereafter the solution is warmed, stirred for 30 minutes, the sodium chloride precipitated is filtered off and washed with anhydrous ethanol. To the combined filtrate 0.554 g (1.000 mmol) of tetrasodium salt and 0.214 g (4.000 mmol) of ammonium chloride and then water is added in an amount dissolving the solid materials. After evaporating the solution, the residue is made free from water at 75° to 80° C. under reduced pressure to give 1.452 g (98.1%) of title product containing 19.91% by weight of sodium chloride and 7.33% by weight of water. A pure chloride-free product can be prepared by extraction with anhydrous ethanol.

$^1$H-NMR spectra of the chloride-free and sodium chloride-containing product (200 MHz, $D_2O$, δ ppm) are identical: 3.90 (4H, broad m); 3.73 (14H, broad m); 2.92 (4H, broad t); 2.72 (4H, broad t).

EXAMPLE 8

Preparation of N,N'-bis(dicarboxymethyl)-1,4,10,13-tetraoxa-7,16-diazacyclooctadecane calcium complex calcium salt After neutralizing 1.743 g (9.53 mmol) of 2-bromomalonic acid in 2.0 ml of water by adding calcium hydroxide in portions in the presence of phenolphthalein indicator, 1.000 g (3.81 mmol) of 1,4,10,13-tetraoxa-7,16-diazacyclooctadecane is added. The reaction mixture is heated at 40°, 45° and finally at 50° C. for a total of 72 hours, then the reaction mixture is heated at 60° C. for 24 hours while portionwise adding 0.85 g (11.47 mmol) of calcium hydroxide under vigorous stirring. Then, the precipitate (the major part of which is calcium hydroxymalonate) is filtered off and washed with 4 to 5 ml of water in 3 portions. The combined filtrate is evaporated under reduced pressure and then 2×35 ml of methylene chloride are distilled off from the evaporation residue to obtain a solid product which is dried at 75° to 85° under reduced pressure. In this way the title product is obtained in a yield of 2.710 g (89.7%) with a calcium bromide content of 31.5% by weight.

The $^1$H-NMR spectrum of this product (200 MHz, $D_2O$, δ ppm) is identical with that of the product prepared according to Example 5. IR spectrum (KBr, cm$^{-1}$): 2920, 2880 (m, $\gamma_{C-H}$); 1615 (vs, $\gamma_{COO/as}$); 1450 (m, $\gamma_{COO/s}$). Other characteristic but unidentified frequencies: 1355 (m), 1290 (m), 1250 (m), 1085 (vs), 950 (m).

EXAMPLE 9

Preparation of N,N'-bis(dicarboxymethyl)-1,4,10,13-tetraoxa-7,16-diazacyclooctadecane iron(II) complex disodium salt The process described in Example 4 is followed by using 0.747 g (1.35 mmol) of product prepared according to Example 1 b) and 0.268 g (1.35 mmol) of ferrous chloride tetrahydrate, except that the oxidation of ferrous ions to ferric ions is prevented during the preparation is prevented by using nitrogen atmosphere. In this way the title product is obtained in a yield of 0.835 g (91.0%) with a sodium chloride content of 17.16% by weight.

The $^1$H-NMR spectrum of the product cannot be evaluated due to the presence of the paramagnetic ferrous ion. IR spectrum (KBr, cm$^{-1}$): 2910, 2880 (m, $\gamma_{C-H}$); 1630 (vs, $\gamma_{COO/as}$); 1400 (s, $\gamma_{COO/s}$). Other characteristic but unidentified frequencies: 1355 (m), 1330 (m), 1100 (s), 930 (m).

EXAMPLE 10

Preparation of N,N'-bis(dicarboxymethyl)-1,4,10,13-tetraoxa-7,16-diazacyclooctadecane zinc complex disodium salt The process described in Example 4 is followed by using 0.735 g (1.32 mmol) of product prepared according to Example 1 b) and 0.180 g (1.32 mmol) of anhydrous zinc chloride to give 0.89 g (97.5%) of title product containing 16.92% by weight of sodium chloride.

$^1$H-NMR spectrum (200 MHz, $D_2O$, δ ppm): 3.6–4.2 (18H, broad t band system); 3.10 (8H, broad t).

EXAMPLE 11

Preparation of N,N'-bis(dicarboxymethyl)-1,4,10,13-tetraoxa-7,16-diazacyclooctadecane trisodium salt 1.72 ml of hydrochloric acid solution of 1.048 mole/liter concentration are added to a solution of 1.000 g (1.804 mmol) tetrasodium salt obtained according to Example 1 b) in 5.0 ml water under cooling (at 0° to 5° C.), then the solution is evaporated, the residue is made free from water by using methylene chloride then is dried at 60° C. under reduced pressure to give 1.069 g (96.7%) of title product containing 9.5% by weight of sodium chloride.

$^1$H-NMR spectrum (200 MHz, D$_2$O, δ ppm): 4.18 (2H, s); 3.79 (16H, m, broad); 3.29 (8H, broad s). The spectrum of the product taken up in D$_2$O in the presence of NaOD is in agreement with the spectrum given in Example 1 b). IR spectrum (KBr, cm$^{-1}$): 2940, 2850, (m; $\gamma_{C-H}$); 1655, 1605 (vs, $\gamma_{COO/as}$); 1400 (m, $\gamma_{COO/s}$). Other characteristic but unidentified frequencies: 1345 (s), 1320 (s), 1120 (s), 1100 (s); 930 (m).

EXAMPLE 12

Preparation of N-dicarboxymethyl-N'-(1,1'-dicarboxyethyl)-1,4,10,13-tetraoxa-7,16-diazacyclooctadecane tetrasodium salt After neutralizing 3.003 g (15.25 mmol) of bromomethylmalonic acid in 0.5 ml of water by adding sodium hydroxide solution of 8.360 mole/liter concentration at 0° to 5° C. in the presence of phenolphthalein indicator, 2.000 g (7.62 mmol) of 1,4,10,13-tetraoxa-7,16-diazacyclooctadecane are added. The solution is maintained at 20° to 25° C. for 8 to 10 days while portionwise adding 1.82 ml (15.25 mmol) of sodium hydroxide solution of 8.360 mole/liter concentration. After termination of the reaction, the mixture is stirred at 55° to 60° C. for 30 minutes, then evaporated. The dry residue is extracted in several portions with a total volume of 25 to 30 ml of methylene dichloride. After evaporating the extract, the residue is treated with ether and the solid precipitate is filtered of. The material remaining after the extraction with ether contains also a little amount of 1,4,10,13-tetraoxa-7,16-diazacyclooctadecane which can be removed by dissolving the product in methylene dichloride and precipitating by ether. In this way a purified N-(1,1'-dicarboxyethyl)-1,4,10,13-tetraoxa-7,16-diazacyclooctadecane disodium salt containing 13.81% by weight of sodium bromide (intermediate) is obtained in a yield of 1.390 g (37.2%).

After evaporation of the ethereal extract 1.159 g of pure 1,4,10,13-tetraoxa-7,16-diazacyclooctadecane are recovered. Thus, the actual yield of the reaction corresponds to 38.5%. $^1$H-NMR spectrum of the intermediate (200 MHz, D$_2$O, δ pm): 3.66 (16H, m); 2.82 (4H, t); 2.72 (4H, t); 1.36 (3H, s).

By using the above intermediate the disubstituted derivative is obtained as follows.

After neutralizing 0.483 g (2.64 mmol) of 2-bromomalonic acid in 0.5 ml of water by adding sodium hydroxide solution of 8.360 mole/liter concentration in the presence of phenolphthalein indicator, 1.002 g (2.04 mmol) of the above intermediate containing 13.81% by weight of sodium bromide are added, then the reaction mixture is maintained at 30° to 45° C. for 72 hours and at 50° to 60° C. for 24 hours while portionwise adding 0.32 ml (2.64 mmol) of sodium hydroxyde solution of 8.360 mole/liter concentration. After termination of the reaction the solution is evaporated and the residue is dried at 75° to 80° C. under reduced pressure. After extracting the dry residue with anhydrous ethanol, the ethanolic extract is evaporated to dryness under reduced pressure and dried to give 1.323 g (83.0%) of the double salt formed with 2.06 moles of sodium bromide.

A sodium bromide-free product can be obtained from the double salt by extraction with 96% by volume of ethanol as described in Example 1 b) to give 0.532 g (54.5%) of the title product.

The $^1$H-NMR and IR spectra of the double salt are practically identical with those of the title product. IR spectrum (KBr, cm$^{-1}$): 2960, 2870 (m, $\gamma_{C-H}$); 1645, 1600 (vs, $\gamma_{COO/as}$); 1405, 1440 (m, $\gamma_{COO/s}$). Other characteristic but unidentified frequencies: 1355 (s), 1315 (s), 1095 (s), 930 (m). $^1$H-NMR spectrum (200 MHz, D$_2$O, δ ppm): 3.89 (1H, s); 3.68 (16H, m); 2.92 (4H, t); 2.78 (4H, t); 1.41 (3H, s).

EXAMPLE 13

Preparation of N-dicarboxymethyl-N'-(1,1'-dicarboxypropyl)-1,4,10,13-tetraoxa-7,16-diazacyclooctadecane tetrasodium salt sodium bromide double salt The process described in Example 12 is followed by using 1.608 g (7.62 mmol) of 2-bromoethylmalonic acid and 1.000 g (3.81 mmol) of 1,4,10,13-tetraoxa-7,16-diazacyclooctadecane to give 0.517 g (26.2%) of N-(1,1'-dicarboxypropyl)-1,4,10,13-tetraoxa-7,16-diazacyclooctadecane disodium salt containing 15.61% by weight of sodium bromide.

After evaporation of the ethereal extract 0.508 g of 1,4,10,13-tetraoxa-7,16-diazacyclooctadecane are recovered. Thus the actual yield is 53.3%. $^1$H-NMR spectrum of the intermediate (200 MHz, D$_2$O, δ ppm): 3.68 (16H, m); 2.88 (4H, t); 2.82 (4H, t); 1.84 (2H, q); 0.90 (3H, t).

The title double salt containing 3.10 moles of sodium bromide is obtained in a yield of 0.475 g (52.7%) by using 0.517 g (1.00 mmol) of the above intermediate containing 15.61% by weight of sodium bromide and 0.229 g (1.20 mmol) of 2-bromomalonic acid.

$^1$H-NMR spectrum of the title double salt (200 MHz, D$_2$O, δ ppm): 3.88 (1H, s); 3.67 (16H, m); 2.91 (4H, t); 2.86 (4H, t); 1.84 (2H, q); 0.88 (3H, t).

EXAMPLE 14

Preparation of N-dicarboxymethyl-N'-(benzyl-dicarboxymethyl)-1,4,10,13-tetraoxa-7,16-diazacyclooctadecane tetrasodium salt containing disodium hydroxymalonate The process described in Example 12 is followed, except that the reaction is carried out in a water/ethanol mixture of 1:1 volume ratio by using 2.081 g (7.62 mmol) of 2-bromo-2-benzylmalonic acid and 1.000 g (3.81 mmol) of 1,4,10,13-tetraoxa-7,16-diazacyclooctadecane to obtain 0.372 g (17.4%) of N-(benzyl-dicarboxymethyl)-1,4,10,13-tetraoxa-7,16-diazacyclooctadecane disodium salt containing 11.21% by weight of sodium bromide (intermediate).

After evaporation of the ethereal extract 0.714 g of 1,4,10,13-tetraoxa-7,16-diazacyclooctadecane are recovered. Thus, the actual yield becomes 60.9%.

$^1$H-NNR spectrum of the intermediate (200 MHz, D$_2$O, δ ppm): 7.45 (2H, d); 7.29 (3H, m); 3.68 (12H, m); 3.57 (4H, t); 3.47 (2H, s); 2.78 (8H, m).

The title double salt containing 0.42 mole of disodium hydroxymalonate is obtained by using 0.372 g (0.662 mmol) of the above intermediate containing 11.21% by weight of sodium bromide and 0.161 g (0.880 mmol) of 2-bromomalonic acid. For obtaining the product, first an extraction with methylene chloride and then extraction with abs. ethanol are carried out to give the title salt in a yield of 0.432 g (91.4%).

$^1$H-NMR spectrum of the title product (200 MHz, $D_2O$, δ ppm): 7.43 (2H, d); 7.29 (3H, m); 3.90 (1H, s); 3.64 (16H, broad); 3.34 (2H, s); 2.91 (4H, t); 2.80 (4H, t).

EXAMPLE 15

Preparation of N,N'-bis(1,1'-dicarboxyethyl)-1,4,10,13-tetraoxa-7,16-diazacyclooctadecane tetrasodium salt After neutralizing 3.11 g (14.79 mmol) of bromomethylmalonic acid dissolved in 1.0 ml of water by adding sodium hydroxide S solution of 0.360 mole/liter concentration at 0° to 5° C. in the presence of phenolphthalein indicator, 3.52 g (6.565 mmol) of N-(1,1'-dicarboxyethyl)-1,4,10,13-tetraoxa-7,16-diazacyclooctadecane disodium salt containing 18.6% by weight of sodium bromide (intermediate) are added, then the reaction mixture is maintained at 20° to 25° C. for 10 to 12 days while portionwise adding 1.77 ml (14.79 mmol) of sodium hydroxide solution of 8.360 mole/liter concentration. Before termination of the reaction, the mixture is heated at 55° to 60° C. for 30 minutes and then evaporated. The dry residue is extracted in several portions with a total of 45 to 50 ml of methylene chloride. The extract is evaporated, the residue is treated with ether, the precipitate is filtered off and dried. in this way 2.08 g (4.29 mmol) of intermediate containing 14.0% by weight of sodium bromide are recovered which can be used in a next manufacturing batch.

The solid material remaining after the extraction with methylene chloride is dried to 75° to 80° C. under reduced pressure. After extraction of the dry residue with 55 to 60 ml of anhydrous ethanol, the ethanolic extract is evaporated to dryness under reduced pressure and dried to give 3.90 g (22.2%) of double salt containing 78.2% by weight of sodium bromide. The yield calculated for the intermediate used up in the reaction is 64.3%.

$^1$H-NMR spectrum of the double salt (200 MHz, $D_2O$, δ ppm): 3.67 (8H, s); 3.64 (8H, t); 2.73 (8H, t); 1.36 (6H, s).

A sodium bromide-free product is obtained from 3.90 g of double salt containing 78.2% by weight of sodium bromide by extraction with 96% by volume ethanol as described in Example 1 b). In this way 0.489 g (57.5%) of title product is obtained.

After evaporation and drying and a repeated extraction with anhydrous ethanol, a double salt containing 80 to 90% by weight of sodium bromide is obtained from the filtrate containing 96% by volume ethanol. This double salt can be utilized in a next manufacturing batch.

1H-NNR spectrum of the title product (200 MHz, $D_2O$, δ ppm): 3.70 (16H, broad m); 2.71 (8H, coalesced t); 1.34 (6H, broadened s).

EXAMPLE 16

Preparation of N,N'-bis(benzyl-dicarboxymethyl)-1,4,10,13-tetraoxa-7,16-diazacyclooctadecane tetrasodium salt sodium bromide double salt The process described in Example 15 is followed; by carrying out the reaction with 0.362 g (1.324 mmol) of 2-bromo-2-benzylmalonic acid and 0.372 g (0.662 mmol) of monosubstituted intermediate containing 11.21% by weight of sodium bromide in a water/ethanol mixture of 1:1 volume ratio, a double salt containing 4.2 moles of sodium bromide is obtained in a yield of 0.085 g (11.1%).

0.296 g of intermediate containing 11.21% by weight of sodium bromide is recovered. Thus, the yield calculated for the intermediate used up in the reaction is 54.2%.

1H-NNR spectrum of the title product (200 MHz, $D_2O$, δ ppm): 7.64 (4H, d); 7.45 (6H, m); 3.65 (12H, m); 3.52 (4H, t); 3.31 (4H, s); 2.68 (8H, t).

EXAMPLE 17

The acute toxicity values of the products prepared according to Examples 1 to 16 were determined on laboratory mice and rats in the following manner.

Solutions containing the compounds in various concentrations were prepared by using physiological saline solution or glucose solution of 5% by weight concentration and the active agents were administered in various concentrations into the blood circulation of the animals by injecting them slowly during 3 to 5 minutes. Groups consisting of 6 to 10 animals (Swiss mice and Wistar rats of both sexes) each were used for the various dose levels. Thereafter, the animals were observed for 30 days. The $LD_{50/30}$ value (i.e. the dose causing the death of 50% of the experimental animals within 30 days) was determined from the number of animals died during this period by using probit analysis/D. J. Finney: Probit Analysis (2nd ed.) Cambridge University Press (1952)/. These values expressed in mmol/kg of body-weight for the active agents according to the invention are summarized in column (B) of Table 1.

TABLE 1

| Characteristic data of the products according to the invention | | | |
|---|---|---|---|
| (A) Example No. | (B) Acute toxicity $LD_{50/30}$ mmol/kg | (C) F factor | (D) EI value |
| 1/a | 0.327 | 1.8 | 5.40 |
| 1/b | 0.379 | 2.8 | 9.66 |
| 2 | 0.368 | 3.3 | 11.10 |
| 3/a | 0.333 | 2.3 | 12.30 |
| 3/b | 0.272 | 1.7 | 8.90 |
| 4 | 0.211 | 2.3 | 7.30 |
| 5 | above 2.5 | 3.7 | 145.00 |
| 6/a | above 3.0 | 3.9 | 158.00 |
| 6/b | above 3.0 | 4.2 | 160.00 |
| 7 | above 2.5 | 1.7 | 65.00 |
| 8 | above 1.5 | 1.6 | 58.00 |
| 9 | 0.250 | 1.7 | 8.25 |
| 10 | 0.091 | 2.3 | 3.20 |
| 11 | 0.111 | 2.6 | 2.90 |
| 12 | 0.305 | 1.5 | 7.90 |
| 13 | 0.302 | 2.1 | 13.30 |
| 14 | 0.422 | 1.4 | 7.60 |
| 15 | 0.450 | 1.3 | 6.80 |
| 16 | 0.470 | 1.3 | 7.10 |

EXAMPLE 18

The radioactive isotope elimination-increasing effects of compounds prepared according to Examples 1 to 16 were compared on Swiss mice as described hereinafter.

An activity of 37 to 74 kBg (1 to 2 μCi) of radioactive strontium ($Sr-85Cl_2$) or radioactive cerium ($Ce-144Cl_3$), respectively, was administered into the abdominal cavity of the animals which were then divided into treatment groups consisting of 5 to 10 animals each. At 30 to 60 minutes after administration of the isotope, the animals of the treated groups were intravenously (i.v.) given the active agent used in an amount to achieve s concentration of 50 to 100 μmol/kg of body-weight in the animal organism for each treatment. The animals of the control groups were similarly treated with the carrier (sterile physiological saline or glucose solution of 5% by weight concentration) without active agent.

Figure 1:
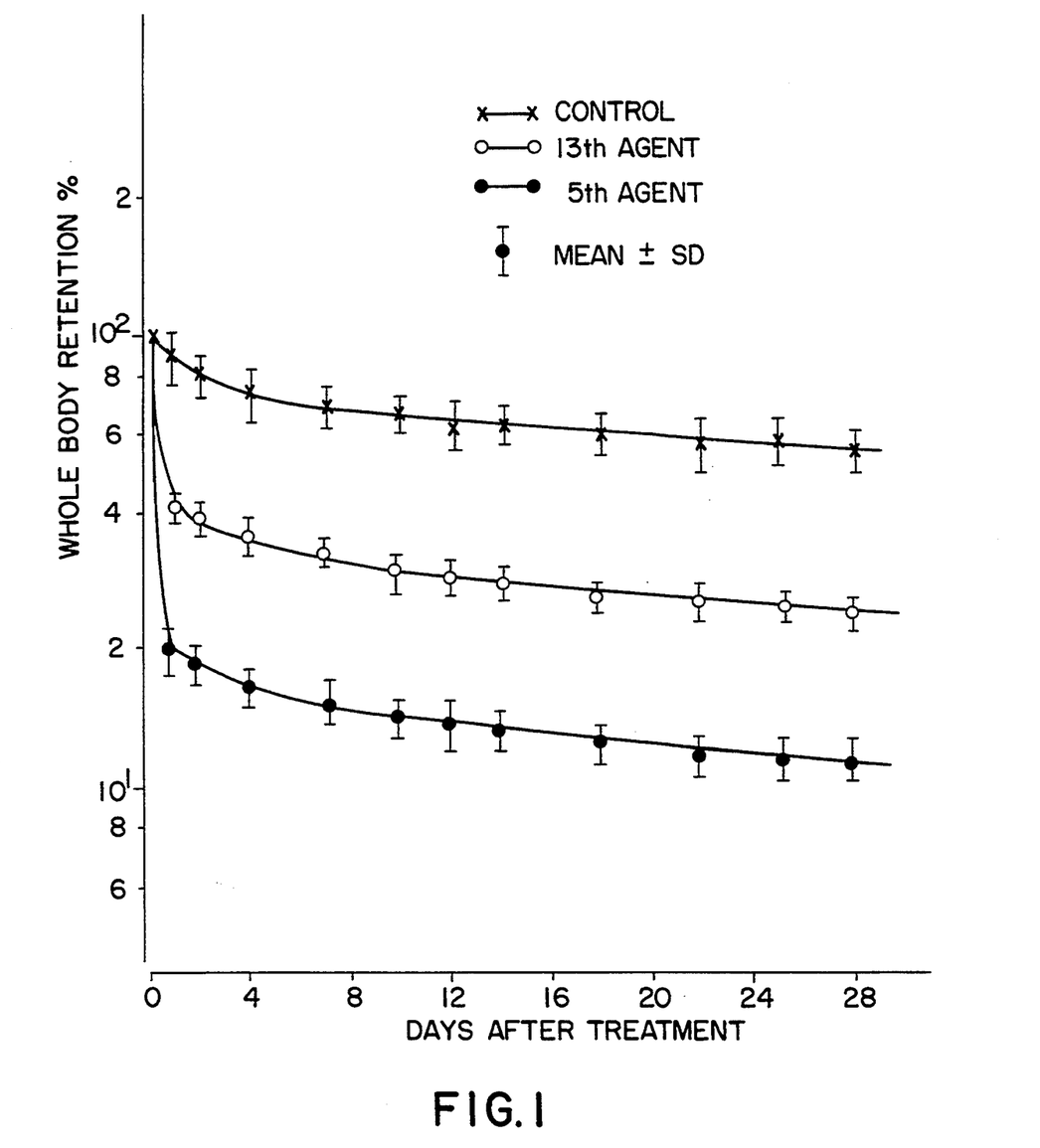
FIG. 1 shows the percentages of metal ions retained in the body, plotted over 28 days after treatment with the compounds of examples 5 and 13, referenced against an untreated control.

The amount of radioactivity introduced to the animal organism was determined immediately after administration of the isotope, thru these measurements were repeated daily or in every two the or three days in a device constructed for the purpose of the whole-body measurements on small animals. The counts observed were related to the starting activity value of the zero (0) day and a so-called retention/time correlation was obtained by considering the activity retained in the organism. The change of activity of the animal organism in the time is illustrated in FIG. 1 where the time (in days) elapsed after the treatment is shown on the abscissa and the whole-body retention as percentage is plotted on the ordinate. It can be seen that the rate of elimination of Sr-85 administered into the abdominal cavity of control animals was slow: within 1 day only 15%, within 4 days 25% and within 7 days 30% of the activity were eliminated from their organism and the elimination was even more delayed in the later period. On the contrary, within 1 day 40%, within 4 days 65% and within 7 days 67% of the radioactivity introduced were excreted from the animal organism after a single treatment with 100 μmol/kg of the active agent prepared according to Example 13. Even more advantageous results were obtained by using the product prepared according to Example 5 which gave elimination values of 81, 84 and 85%, respectively, within the intervals mentioned above. Based on analysis carried out in the above manner, it was stated that the retention curves could be described by a two-component descending exponential function. The F factors and EI values relating to the products according to the Examples mentioned above are summarized in the columns (C) and (D), respectively, of Table 1. It is obvious that the effectivities of various decorporating agents, particularly on the basis of their EI values, are highly different. In our opinion, the agents with an EI value-of 0 to 5 are weak, those with an EI value of 5 to 50 have a medium effect, those with an EI value of 50 to 100 are good and those with an EI value above 100 are excellent.

Figure 2:
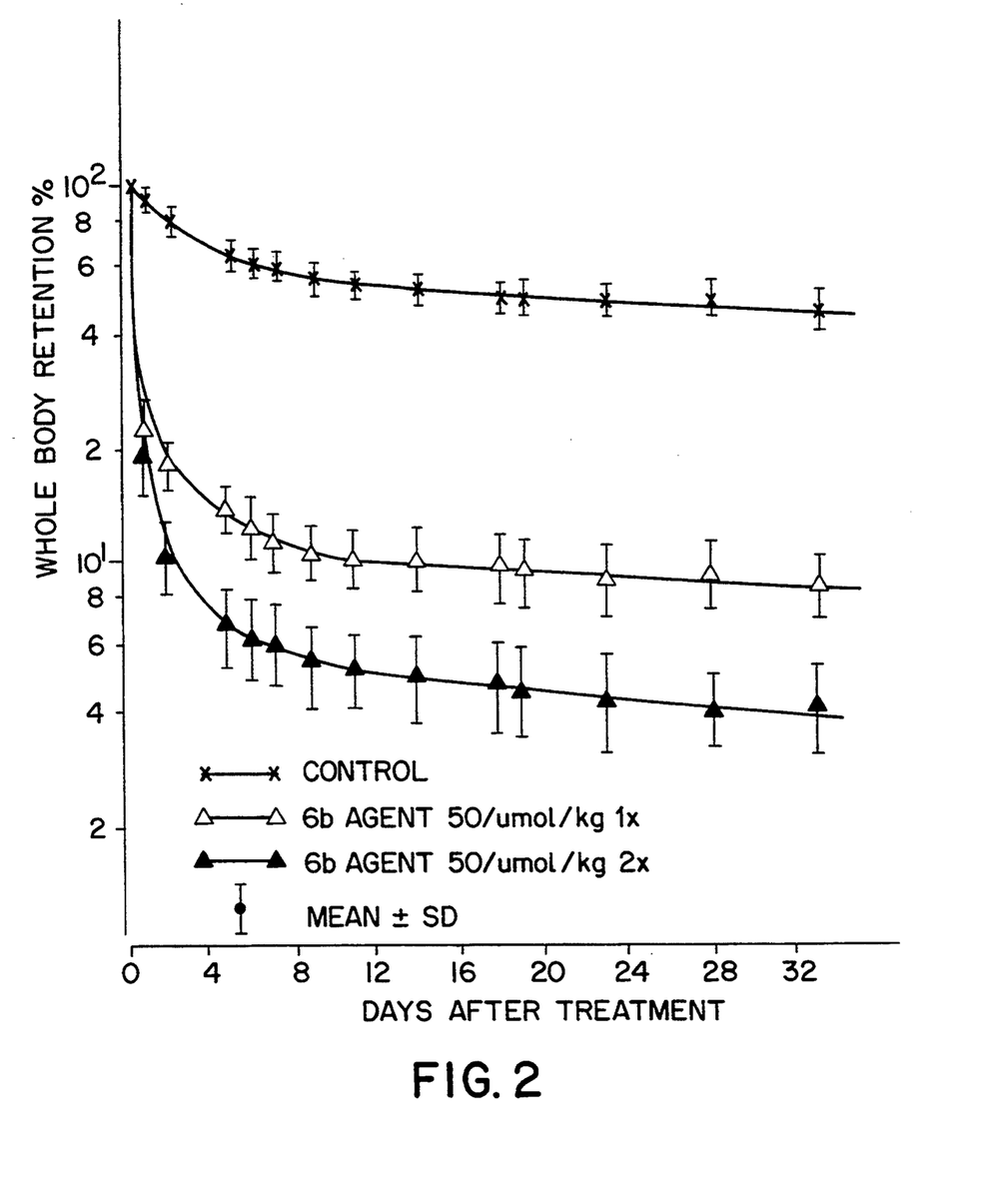
FIGS. 2 & 3 show the percentages of metal ions retained in the body, plotted over 32 days after treatment with compound "b" of example 6 at both full and double strength, referenced against an untreated control.
Figure 3:
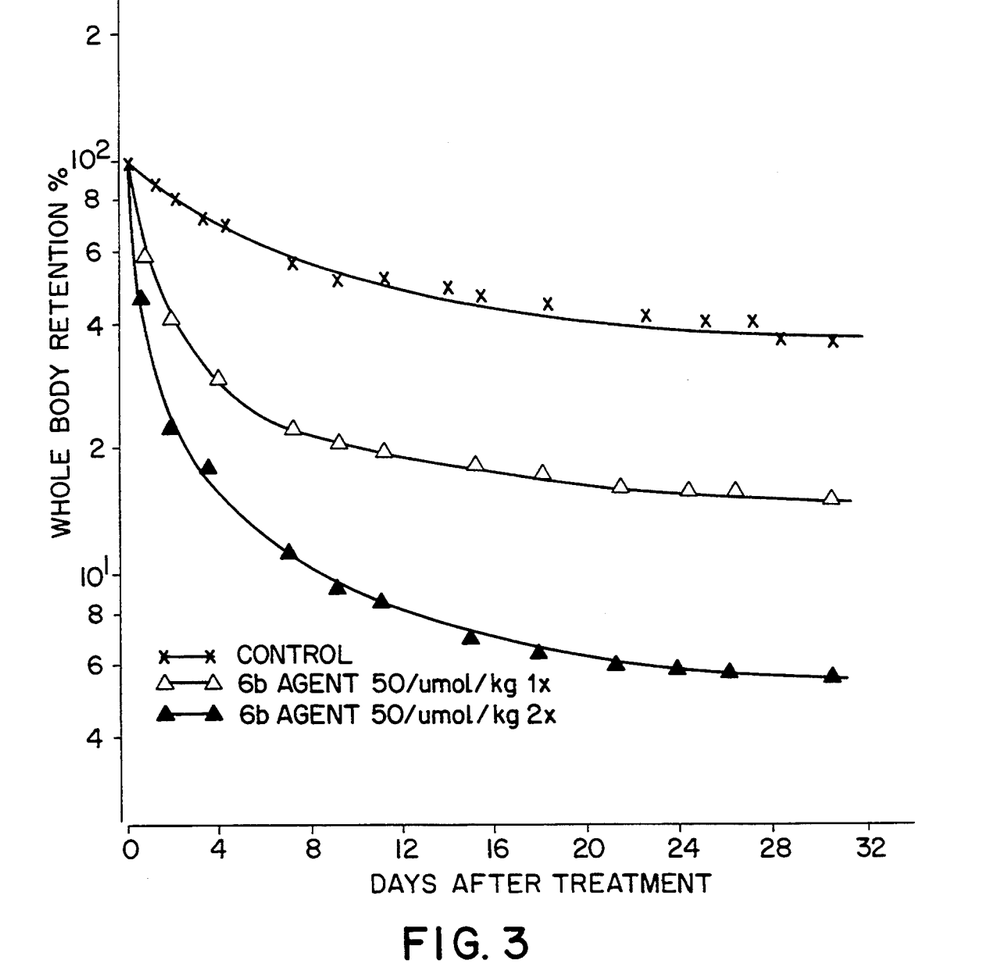
Figure 4A:
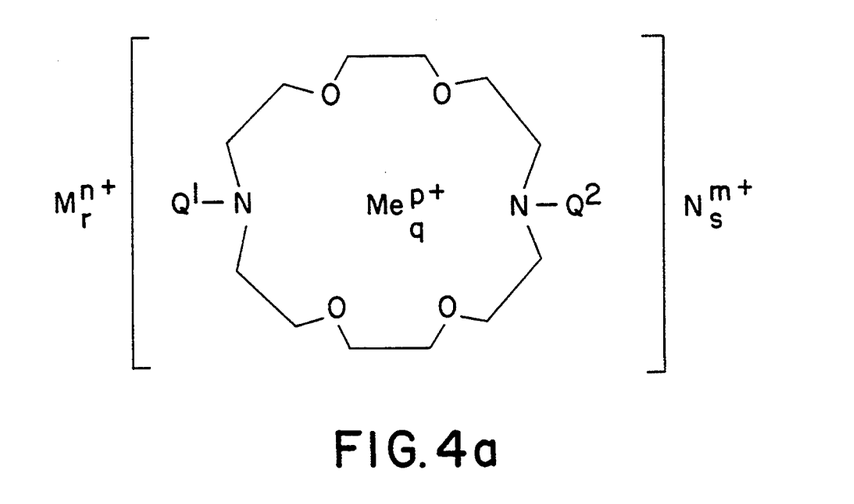
FIG. 4a shows formula (I), as shown on page one and in claim 1.
Figures 4B, 4C:
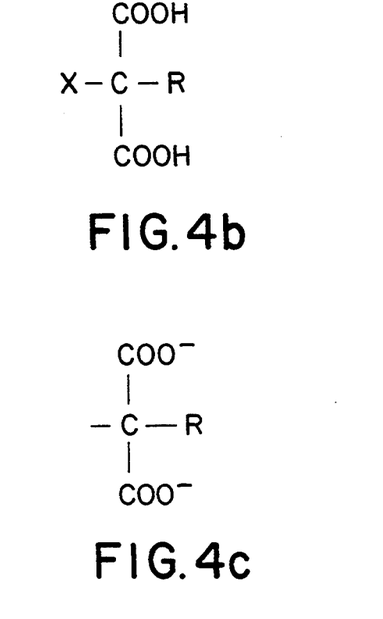
FIG. 4b shows formula (II), as shown on page six and in claim 4.
FIG. 4c shows formula (III), as shown on page one and in claim 1.

EXAMPLE 19 a) The whole-body retention curves illustrated in FIG. 2 show the elimination of radioactive strontium introduced through the trachea into the lungs of Wistar rats after intraperitoneal (i.p.) administration of the compound described in Example 6 b). It can be seen from the pattern of the upper curve of FIG. 2 that the radioactive strontium was eliminated to a low grade from the organism of control animals treated only with the solvent. Not more than 30 to 35% of the starting activity were eliminated in the days following the inner contamination. On the contrary, the whole-body load significantly decreased from 90% (measured on the controls) to 20% both in the group treated once with 50 μmol/kg of body weight of the agent according to the invention (middle curve) or in the group treated twice in 3-hour interval (lower curve) within 1 day following the treatment. The rapid elimination of the isotope was continued in the days following the treatment, and reached 88 to 90% in the once-treated group and 94 to 96% in the twice-treated group. It is also an important experimental result that hardly any or no radioactive strontium could be detected in the bones of the animals treated with the active agent according to the invention and killed at the end of the experiment. The residual activity of 5 to 10% measured as whole-body retention was found in the soft parts and liver of the animals whereas the major part (65 to 70%) of the retention found in the controls were built in to the bones. Similarly advantageous results were obtained by administering the compounds according to the invention in an intravenous route or into the subcutaneous connective tissue.

b) The compounds of the invention increasing the isotope elimination were tried to remove other radioactive metals, firstly cerium-144 (belonging to the group of the rare earth elements) from the animal organism. In this Example the elimination of Ce-144Cl$_3$, introduced to the lungs of female Wistar rats, is illustrated as a function of the time elapsed after a single dose or after a treatment repeated at a 24-hour interval (see FIG. 3). The results obtained prove that the compounds according to the invention can advantageously be used also for the removal of this radioactive compound having a relatively low solubility in body fluids from the lungs. At the end of the experiment, i.e. on the 30th day, 40% of the introduced starting activity were present in the control animals whereas 14% were detected in the group treated i.p. once with the active agent according to the invention; and the whole-body retention decreased to 5.6% on effect of treatments with the active agent by 60 minutes and then by 26 hours after administration of the isotope. The beginning abrupt but later delayed pattern of whole-body retention curves of the treated groups is likely due to solubility relations of the radioactive contaminating compound and the elimination properties of the metal complex.

EXAMPLE 20

The effect of compounds according to the invention on the elimination of isotopes after administration into the blood circulation, abdominal cavity or subcutaneous connective tissue have been described in Example 17 to 19. From the viewpoint of human therapy and even more of the effective and rapid protection of a greater population it was important to justify that the compounds according to the invention are useful to decorporate internal radioisotope contaminations also by other routes of administration.

Wistar rats were used for this purpose. In a part of the examinations radiostrontium was administered into the abdominal cavity of the animals and after 60 minutes the active agent according to the invention was given through the rachea into the lungs. The compounds indicated in Table 1 with an EI value above 100 were used as active agents. Thereafter, the while-body activities were measured for 30 days. It turned out on evaluation of the whole-body retention curves, plotted in the usual manner, that the active agents according to the invention exerted a good effect on the elimination after inhalation in a powder or liquid aerosol form. The retention of 91% measured in the control animals was diminished to 15% on the first day, and became lower than 10% on the 3rd day in the treated animals. An F factor value of 7.9 and EI value of 164 (c.f. Table 1) were found which supported the above statements.

The possibility of adsorption of the active agents according to the invention from the epithelial surface was studied in additional experiments. A 3×3 cm area of the dorsal skin of rats was depilated. After administering radioactive strontium through the trachea into the lungs of the anaesthetized animals, whole-body activities were measured, then the active agent was applied in solution on the dorsal skin area previously depilated and cleaned. The area containing the active agent was covered with an adhesive plaster. It could be stated from daily measurements of the whole-body activities that the active agents according to the invention exerted their isotope-mobilizing effect through the skin, too. By considering all the measurement values, an F factor value of 2.5 and EI value of 105 to 110 were obtained.

On the basis of the above experimental results the active agents according to the invention can be used also in the form of pharmaceutical compositions such as sublingual tablet, suppository, enterosolvent dragée or capsule or transdermal plaster.

We claim:

1. A compound of the formula (I)

wherein $Q^1$ and $Q^2$ stand for a group of the formula (III)

the group of the formula (III)

R substituents independently represent hydrogen, a $C_{1-5}$ straight or branched chain alkyl group, a $C_{2-5}$ straight or branched chain alkenyl group, phenyl or phenyl-$C_{1-5}$-alkyl group, the phenyl groups being optionally being substituted on their aromatic part by one or more halogen(s), $C_{1-5}$-alkyl, $C_{1-5}$-alkoxy, cyano or nitro group(s);

Me stands for an alkaline metal or alkaline earth metal or transition metal ion;

q is 0 or 1;

M and N, independently from each other, stand for hydrogen or an alkaline metal, alkaline earth metal or optionally substituted ammonium ion;

m, n and p are integers each being equal to the charge of M, N or Me, respectively;

s and r are, independently from each other, 0, 1,2,3, or 4, with the proviso that
  (i) r, s and q cannot simultaneously be 0;
  (ii) the number of hydrogens in the meaning of M or N may be 0, 1 or 2;
  (iii) q is 1 when R means hydrogen; and
  (iv) M and N are other than sodium or lithium ions when q is 0.

2. A compound of the formula (I) as claimed in claim 1, wherein $Q^1$ and $Q^2$ are the same and R means hydrogen.

3. N,N'-bis(dicarboxymethyl)-1,4,10,13-tetraoxa-7,16-diazacyclooctadecane calcium complex disodium salt.

* * * * *

UNITED STATES PATENT AND TRADEMARK OFFICE
CERTIFICATE OF CORRECTION

PATENT NO.: 5,440,031

DATED: August 8, 1995

INVENTOR(S): VARGA et al.

It is certified that error appears in the above-identified patent and that said Letters Patent is hereby corrected as shown below:

Item [57], delete the abstract shown and replace with the following:

-- Abstract of the Disclosure
Metal complexes, salts and double salts of 1,4,10,13-tetraoxa-7,16-diazacyclooctadecane compounds of the formula (I), wherein $Q^1$ and $Q^2$ mean a group of the formula (III), where
R  is H, a $C_{1-5}$ straight or branched chain alkyl group, a $C_{2-5}$ straight or branched chain alkenyl group, phenyl or phenyl-$C_{1-5}$alkyl group, with the proviso that at least one of $Q^1$ and $Q^2$ is other than hydrogen;
Me is an alkaline metal, alkaline earth metal or transition metal ion;
q  is 0 or 1;
M and N, independently from each other are hydrogen, an alkaline metal, alkaline earth metal or optionally substituted ammonium ion;

UNITED STATES PATENT AND TRADEMARK OFFICE
CERTIFICATE OF CORRECTION

PATENT NO.: 5,440,031

DATED: August 8, 1995

INVENTOR(S): VARGA et al.

It is certified that error appears in the above-identified patent and that said Letters Patent is hereby corrected as shown below:

m, n and p are integers each being equal to the charge of M, N or
    Me, respectively;
s are r are, independently from each other, 0, 1, 2, 3 or 4, with
    the proviso that
        (i) r, s and q can not simultaneously be 0; and
        (ii) the number of hydrogens in the meaning of M or N may be
        0, 1 or 2,
as well as pharmaceutical compositions containing these compounds.--

Column 18, claim 1, line 7, before "the group of the formula (III)" insert
    --and in--.

Signed and Sealed this

Sixteenth Day of January, 1996

*Attest:*

BRUCE LEHMAN

*Attesting Officer*      Commissioner of Patents and Trademarks